United States Patent
Minnigh et al.

(10) Patent No.: US 8,019,625 B2
(45) Date of Patent: Sep. 13, 2011

(54) ADMINISTRATIVE REPORTS FOR DIGITAL RADIOLOGY DEPARTMENT

(75) Inventors: Todd Minnigh, Pittsford, NY (US); David A. Kennedy, Webster, NY (US); Delin Shen, Pittsford, NY (US)

(73) Assignee: Carestream Health, Inc., Rochester, NY (US)

( * ) Notice: Subject to any disclaimer, the term of this patent is extended or adjusted under 35 U.S.C. 154(b) by 1072 days.

(21) Appl. No.: 11/759,352

(22) Filed: Jun. 7, 2007

(65) Prior Publication Data

US 2008/0306760 A1 Dec. 11, 2008

(51) Int. Cl.
*G06Q 50/00* (2006.01)
(52) U.S. Cl. .................................. 705/3; 705/2
(58) Field of Classification Search ............... 705/2, 3
See application file for complete search history.

(56) References Cited

U.S. PATENT DOCUMENTS

| | | | |
|---|---|---|---|
| 6,282,513 B1* | 8/2001 | Strawder | 705/2 |
| 2004/0247167 A1* | 12/2004 | Bueno et al. | 382/132 |
| 2005/0209888 A1* | 9/2005 | Oowaki et al. | 705/3 |
| 2005/0213702 A1* | 9/2005 | Akagi | 378/37 |
| 2006/0004870 A1* | 1/2006 | Pomeroy et al. | 707/104.1 |
| 2007/0036268 A1* | 2/2007 | Matsuno | 378/98.2 |
| 2007/0232885 A1* | 10/2007 | Cook et al. | 600/407 |

* cited by examiner

*Primary Examiner* — Lena Najarian (57) ABSTRACT

A system produces administrative reports for a digital radiology department. The system includes a plurality of digital radiographic systems, each of which has storage for storing digital data in html relating to the use and operation of the system. A computer is in communication with the plurality of digital radiographic systems. The computer has a web browser for collecting digital data relating to the operation and/or use of each digital radiographic system. The computer produces one or more administrative reports based on the collected data.

15 Claims, 6 Drawing Sheets

TECH STATISTICS — 70

| TECH ID | AVERAGE EXPOSURE | NUMBER OF ACCEPTS | NUMBER OF REJECTS | PERCENT REJECT |
|---|---|---|---|---|
| 54321 | 1930 | 30 | 3 | 9.1% |
| 98765 | 3050 | 80 | 2 | 2.43% |

TOTALS:

TECH STATISTICS (54321) — 72

| BODY PART | AVERAGE EXPOSURE | NUMBER OF ACCEPTS | NUMBER OF REJECTS | PERCENT REJECT |
|---|---|---|---|---|
| CSPINE | 2060 | 25 | 2 | 7.4% |
| HAND | 1800 | 5 | 1 | 16.66% |
| TOTALS: 2 | 1930 | 30 | 3 | 9.1% |

TECH STATISTICS (54321, CSPINE) — 74

| PROJECTION | EXPOSURE INDEX | EXAM DATE &TIME | ACCESSION NUMBER | REJECT REASON | REJECT COMMENTS |
|---|---|---|---|---|---|
| AP | 2100 | 01/14/2004 13:35:43 | 1446 | PATIENT MOTION | MOVED HEAD |
| LATERAL | 2020 | 01/14/2004 13:37:59 | 1446 | POSITIONING ERR | HEAD FORWARD |

| TECH ID | BODY PART | PROJECTION | EXPOSURE INDEX | EXAM DATE | EXAM TIME | |
|---|---|---|---|---|---|---|
| BEW | CHEST | PA | 1960 | 5/6/2004 | 09:22:57 | Ⓐ |
| BEW | CHEST | LATERAL | 2020 | 5/6/2004 | 09:22:57 | Ⓑ |
| BEW | FACIAL BONES | PA | 2110 | 5/6/2004 | 09:38:10 | Ⓒ |
| BEW | FACIAL BONES | PA | 1980 | 5/6/2004 | 09:38:10 | Ⓓ |
| BEW | CHEST | AP | 2130 | 5/6/2004 | 09:38:10 | Ⓔ |
| BEW | ABDOMEN | AP | 2070 | 5/6/2004 | 09:50:10 | Ⓕ |
| BEW | ABDOMEN | AP | 2050 | 5/6/2004 | 09:50:10 | Ⓖ |
| RMG | CHEST | LATERAL | 1950 | 5/6/2004 | 11:06:25 | Ⓗ |
| RMG | CHEST | PA | 1990 | 5/6/2004 | 11:06:25 | Ⓘ |
| BEW | CHEST | PA | 2000 | 5/6/2004 | 11:16:04 | Ⓙ |
| BEW | CHEST | LATERAL | 1900 | 5/6/2004 | 11:16:04 | Ⓚ |
| MMW | ABDOMEN | AP | 2430 | 5/6/2004 | 11:20:30 | Ⓛ |
| MMW | ABDOMEN | AP | 2410 | 5/6/2004 | 11:20:30 | Ⓜ |
| MMW | CHEST | PA | 1720 | 5/6/2004 | 11:43:58 | Ⓝ |
| MMW | CHEST | LATERAL | 1840 | 5/6/2004 | 11:43:58 | Ⓞ |
| BEW | CHEST | PA | 1950 | 5/6/2004 | 11:44:26 | Ⓟ |
| BEW | CHEST | LATERAL | 1910 | 5/6/2004 | 11:44:26 | Ⓠ |

| | SCAN DATE | SCAN TIME | PATIENT ID | ACCESSION NUMBER | REJECT COMMENTS |
|---|---|---|---|---|---|
| A | 5/6/2004 | 09:26:16 | 3492139 | 1123474 | |
| B | 5/6/2004 | 09:27:19 | 3492139 | 1123474 | |
| C | 5/6/2004 | 09:38:40 | 103323889 | 1123504 | |
| D | 5/6/2004 | 09:40:16 | 103323889 | 1123504 | |
| E | 5/6/2004 | 09:42:33 | 103323889 | 1123504 | |
| F | 5/6/2004 | 09:52:33 | 3769247 | 1123507 | CLIPPED ANATOMY |
| G | 5/6/2004 | 09:53:39 | 3769247 | 1123507 | |
| H | 5/6/2004 | 11:11:17 | 1970086 | 1123778 | |
| I | 5/6/2004 | 11:12:21 | 1970086 | 1123778 | |
| J | 5/6/2004 | 11:18:12 | 5325378 | 1123803 | |
| K | 5/6/2004 | 11:19:19 | 5325378 | 1123803 | |
| L | 5/6/2004 | 11:20:49 | 2833481 | 1123810 | PATIENT MOTION |
| M | 5/6/2004 | 11:22:03 | 2833481 | 1123810 | |
| N | 5/6/2004 | 11:45:42 | 7328693 | 1123915 | |
| O | 5/6/2004 | 11:46:57 | 7328693 | 1123915 | |
| P | 5/6/2004 | 11:48:09 | 5665344 | 1123920 | |
| Q | 5/6/2004 | 11:49:12 | 5665344 | 1123920 | |

RADIOGRAPHER IMAGE ADJUSTMENTS

| EXAM YEAR | (ALL) ▽ |
| EXAM MONTH | (ALL) ▽ |
| CR UNIT | (ALL) ▽ |

| | | DATA ▽ | | |
|---|---|---|---|---|
| TECH ID ▽ | BODY PARTS ▽ | # EXAMS | % ADJUSTED | EXP. INDEX |
| (BLANK) | CHEST | 11 | 100 % | 1560 |
| | LONG BONES | 40 | 100 % | 1945 |
| (BLANK) TOTAL | | 51 | 100 % | 1886 |
| GRAND TOTAL | | 51 | 100 % | 1886 |

◁ ▷ | IMAGE ADJUSTMENTS / TECH SUMMARY / DELIVERY STATISTICS / DATABASE PAGE

TECH STATISTICS — 70

| TECH ID | AVERAGE EXPOSURE | NUMBER OF ACCEPTS | NUMBER OF REJECTS | PERCENT REJECT |
|---|---|---|---|---|
| 54321 | 1930 | 30 | 3 | 9.1% |
| 98765 | 3050 | 80 | 2 | 2.43% |

TECH STATISTICS (54321) — 72

| BODY PART | AVERAGE EXPOSURE | NUMBER OF ACCEPTS | NUMBER OF REJECTS | PERCENT REJECT |
|---|---|---|---|---|
| CSPINE | 2060 | 25 | 2 | 7.4% |
| HAND | 1800 | 5 | 1 | 16.66% |
| TOTALS: 2 | 1930 | | 3 | 9.1% |

TECH STATISTICS (54321, CSPINE) — 74

| PROJECTION | EXPOSURE INDEX | EXAM DATE & TIME | ACCESSION NUMBER | REJECT REASON | REJECT COMMENTS |
|---|---|---|---|---|---|
| AP | 2100 | 01/14/2004 13:35:43 | 1446 | PATIENT MOTION | MOVED HEAD |
| LATERAL | 2020 | 01/14/2004 13:37:59 | 1446 | POSITIONING ERR | HEAD FORWARD |

FIG. 5

ADMINISTRATIVE REPORTS FOR DIGITAL RADIOLOGY DEPARTMENT

FIELD OF THE INVENTION

This invention relates in general to radiographic systems and more particularly to administrative analysis and reporting of a digital radiology department including a plurality of digital radiographic systems, such as computed radiographic and digital radiographic systems.

BACKGROUND OF THE INVENTION

Conventional analog projection radiography involves projecting a beam of x-radiation through a body part of a patient and recording the projected radiographic image on unexposed film in contact with one or two screens contained in a cassette. The film is then removed from the cassette in a darkroom environment and processed using chemical processing. Cassettes can also be reloaded with unexposed radiographic film in the darkroom. The developed film is then placed on a light box for review and diagnosis by a trained health care professional, such as a radiologist. The typical analog radiography department include ID cameras for exposing patient identification and other information on exposed x-ray film, darkrooms and radiographic film processors, chemical supplies, a water source, processor QA (Quality Assurance) strips, film/screen contact tests, waste film bin, monthly repeat analysis, and dose management supported by a fixed speed system. A typical darkroom needs water, a drain for chemicals, 220V power, ventilation, a safelight, chemical supply, and a film supply.

As with consumer and professional photography, conventional analog film/screen radiography is being supplemented and/or replaced by digital radiographic systems, such as computed radiography (CR) and digital radiography (DR).

The digital radiology department is configured to include the following: CR and DR systems for radiographic image processing, high resolution workstations for reviewing digital radiographic images, test tool phantoms for system analysis. The computer based digital department includes the ability to delete images, the ability to fix images, and allows the use of auto density correction. Patient ID is managed through RIS/HIS (Radiology Information Systems/Hospital Information Systems) interface. Software is available to manage many tasks. Thus, CR and DR will replace film, QA workstations will replace QA lightboxes, barcode scanners will replace ID cameras, PACS or printers will replace processors, and pixel will replace grains of silver. However. technologists will remain the same and patients and diseases will be as usual.

Managing image quality takes a different focus in a digital world in a film environment, any exposure variation is immediately evident managers and technologists in charge of quality control monitor exposure accuracy by analyzing the bin of rejected films and talking to technologists about how to resolve any problems the goal is to reduce repeat exams to eliminate multiple radiation doses for patients while simultaneously improving departmental efficiency. In the digital world, the ability to delete mistakes meant that this valuable tool for tracking and improving the image capture process was lost. It is desirable that there be a solution that allows review of repeated exams and review of exposure levels used from a department-wide perspective, rather than from each individual system. This would give quality managers a convenient snapshot of how individuals are doing. For example, if a student has been working to improve his lateral C-spine images, the manager or educator could view this technologist's repeat analysis results, regardless of which radiographic system was used to make the images.

There is a need in the digital radiology department for administrative analysis and reporting to measure, track and manage performance of people, processes, and devices. There is also a need to manage quality such as, over and under x-ray exposure, x-ray image repeats, and imaging system performance.

SUMMARY OF THE INVENTION

According to the present invention, there is provided a fulfillment of the needs and solution to the problems discussed above.

According to an aspect of the present invention there is provided a system for producing administrative reports for a digital radiology department comprising: a plurality of digital radiographic systems, each of which has storage for storing digital data in html relating to the operation and/or use of said system; and a computer which is in communication with said plurality of digital radiographic systems, wherein said computer has a web browser for collecting digital data relating to the operation and/or use of each said digital radiographic systems, and wherein said computer produces one or more administrative reports based on said collected data.

The invention has the some advantages. For example, in a digital radiology department, the department administrator can measure, track and manage performance of people, processes, and digital radiographic systems. Also, an administrator can manage image quality, such as over and under exposure, x-ray image repeats, and imaging system performance.

DETAILED DESCRIPTION OF THE INVENTION

Figure 1:
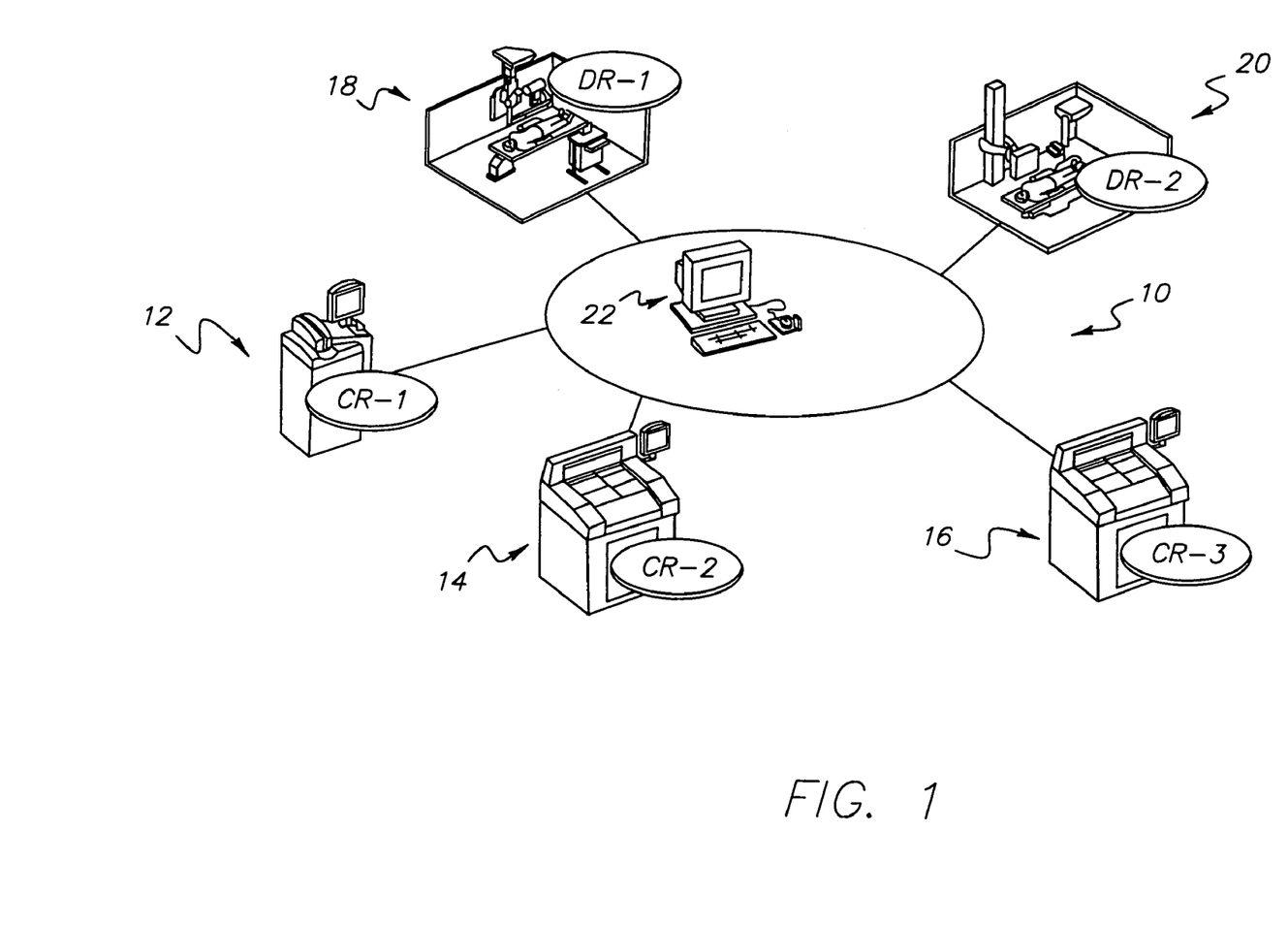
FIG. 1 is a diagrammatic view of a digital radiology department incorporating the present invention.

Referring to FIG. 1, there is shown a diagrammatic view of a digital radiology department incorporating the present invention. As shown, digital radiology department 10 includes a plurality of digital radiographic systems, including computed radiographic systems 12, 14, and 16 (CR1, CR2, CR3) and digital radiographic systems 18 and 20 (DR1, DR2). In general, computed radiography involves the exposure of a patient's body part to x-radiation and recording the x-ray image on a reusable imaging plate contained in a cassette. The cassette is brought to a computed radiography reader where the exposed imaging plate is removed from the cassette, and is scanned by a laser beam to produce a digital radiographic image, which is available for viewing on a high resolution electronic display. The imaging plate is erased, returned to the cassette, and is available for further imaging. Systems 12-16 depict the CR reader. Direct radiography involves the exposure of a patient's body part to x-radiation on an imaging sensor which converts the x-ray image directly into a digital radiographic image which is immediately viewable on a high resolution electronic display. Systems 18 and 20 depict complete x-ray systems. Systems 12-20 are in communication with a central computer 22 depicted as a desktop workstation. Communication can be by way of known wired or wireless communication technologies. CR and DR systems are known, for example, from Carestream Health, Inc. of Rochester, N.Y.

Computer 22 can be any type of computer and typically has one or more processors for processing digital data; digital data storages devices such as magnetic hard drives, magnetic tape drives, optical disc and tape drives, solid state storages devices and the like for storing digital data; input devices such as a keyboard, a mouse, remote optical or electromagnetic controllers; output devices, such as an electronic display and printer; and software for operating the computer and for storing applications that can be processed by the computer. Each of systems 12-20 include or are attached to digital data storage devices for storing digital data in html that relate to the operation and/or use of the system. These storage devices are in communication with computer 22.

Digital data stored at each digital radiographic system can include the following: in general, repeat analysis data, exposure level data, device usage data, and equipment quality data; more specifically, system use by radiographer, exam mix by radiographer, exam mix by system, exam type by system, CR cassette usage, CR cassette history, rejected exams by radiographer, repeat analysis by radiographer repeat analysis by exam type, repeat images by exam and by technologist, reject reasons, reject comments, exposure index statistics by radiographer and exam type, radiographer image adjustments, and image delivery statistics, among other data. This may also include collection of device specific performance data and system diagnostic information, including, but not limited to, Modulation Transfer Function (MTF) data, Detective Quantum Efficiency (DQE) data, Flat Field consistency data, System Linearity data, pixel dropout data, and system sensitivity data.

Figure 2:
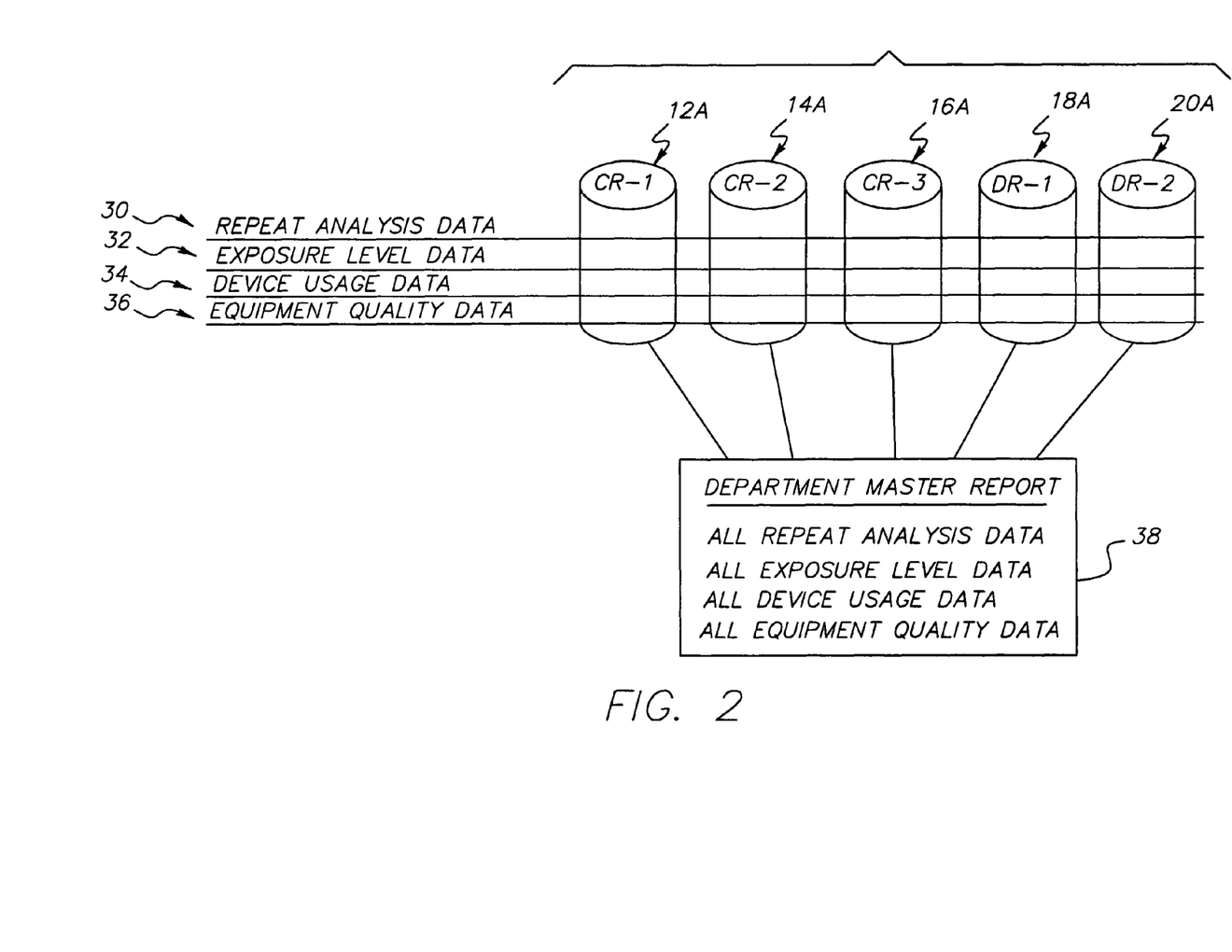
FIG. 2 is a diagrammatic view illustrating the present invention.

FIG. 2 diagrammatically shows storage devices 12A-20A of respective systems 12-20. The legends 30-36 on the left hand side of the figure illustrate data stored in digital data storage devices 12A-20A as Repeat Analysis Data, Exposure Level Data, Device Usage Data, and Equipment Quality Data. According to the present invention, computer 22 has a web browser and a web crawler that collects data from each radiographic system and produces one or more reports based on the collected data. As an example, the illustrated Department Master Report 38 includes All Repeat Analysis Data, All Exposure Level Data, All Device Usage Data, and All Equipment Quality Data. The report can be displayed on a computer electronic display or printed out as hard copy by a printer.

Figures 3, 3A:
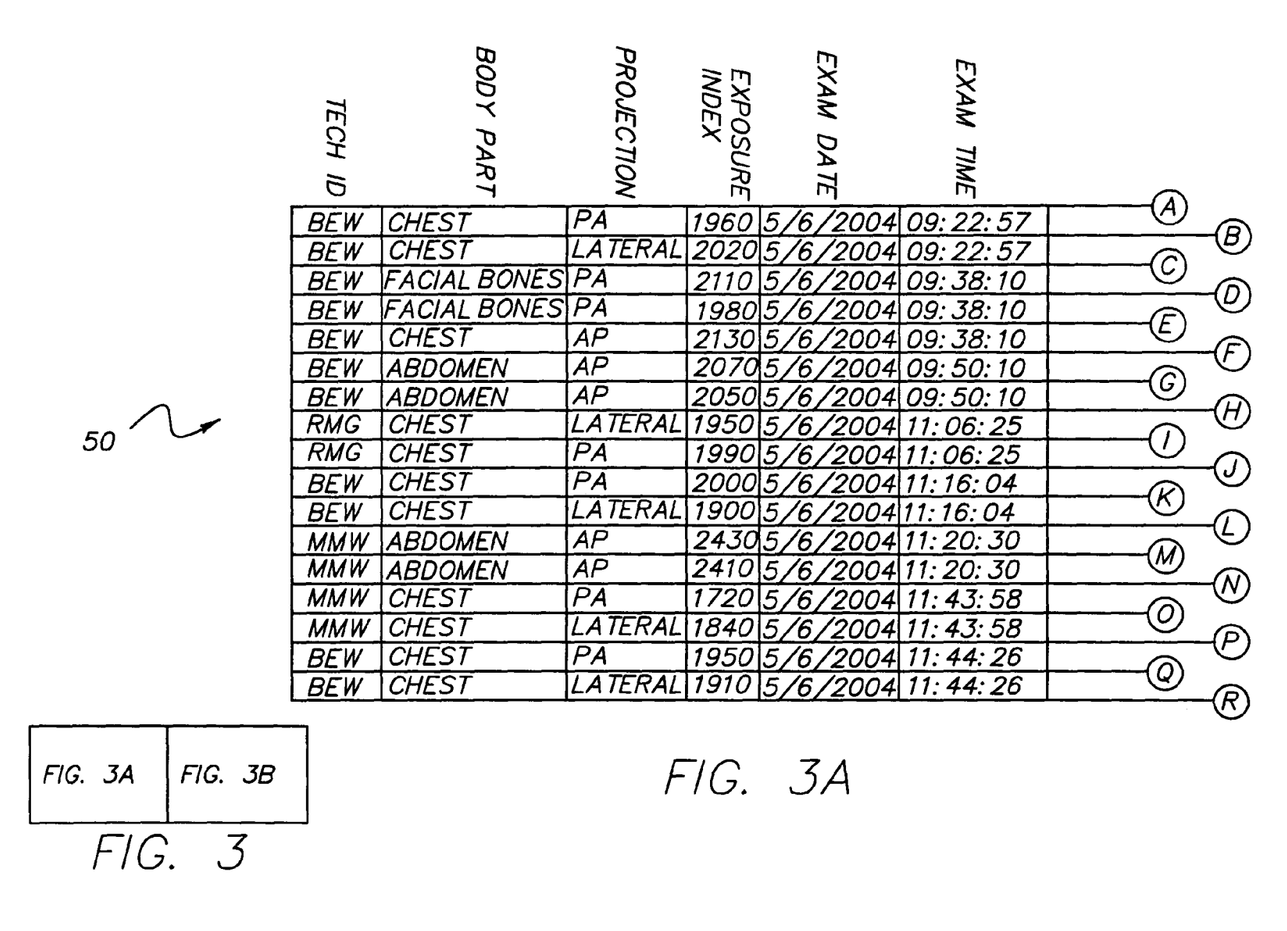
FIGS. 3A-3B are diagrammatic views of a sample report illustrating the logging of CR and DR exposure index.
Figure 3B:
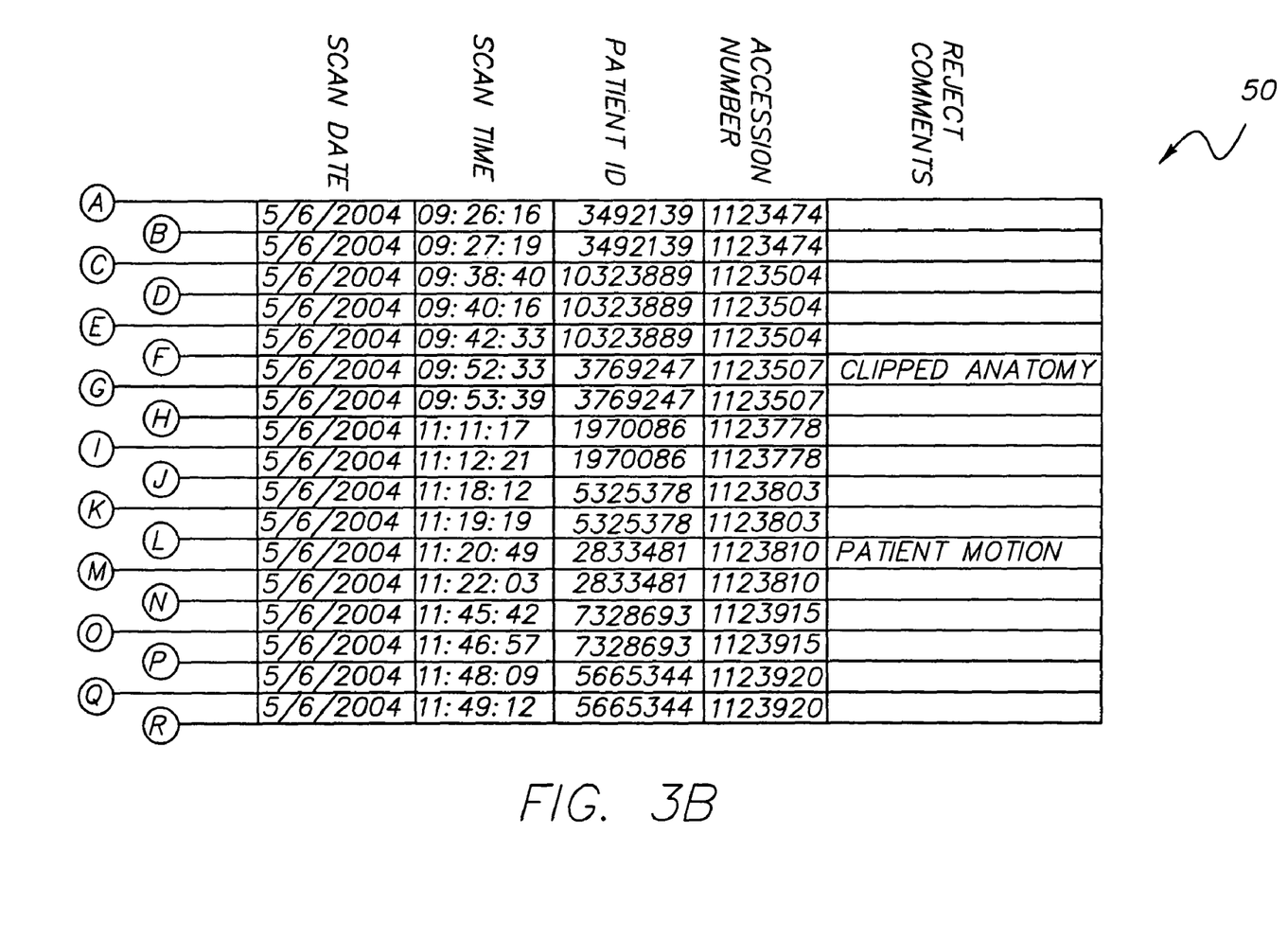

FIG. 3 shows a sample CR and DR Exposure Index Logging report 50 produced by the present invention detailing the technologist's ID, the body part and projection of the x-ray exam, the exposure index of the exam, the exam date and time, the scan date and time, the patient ID, the accession number and any reject comment necessitating the repeat of the exam.

Figure 4:
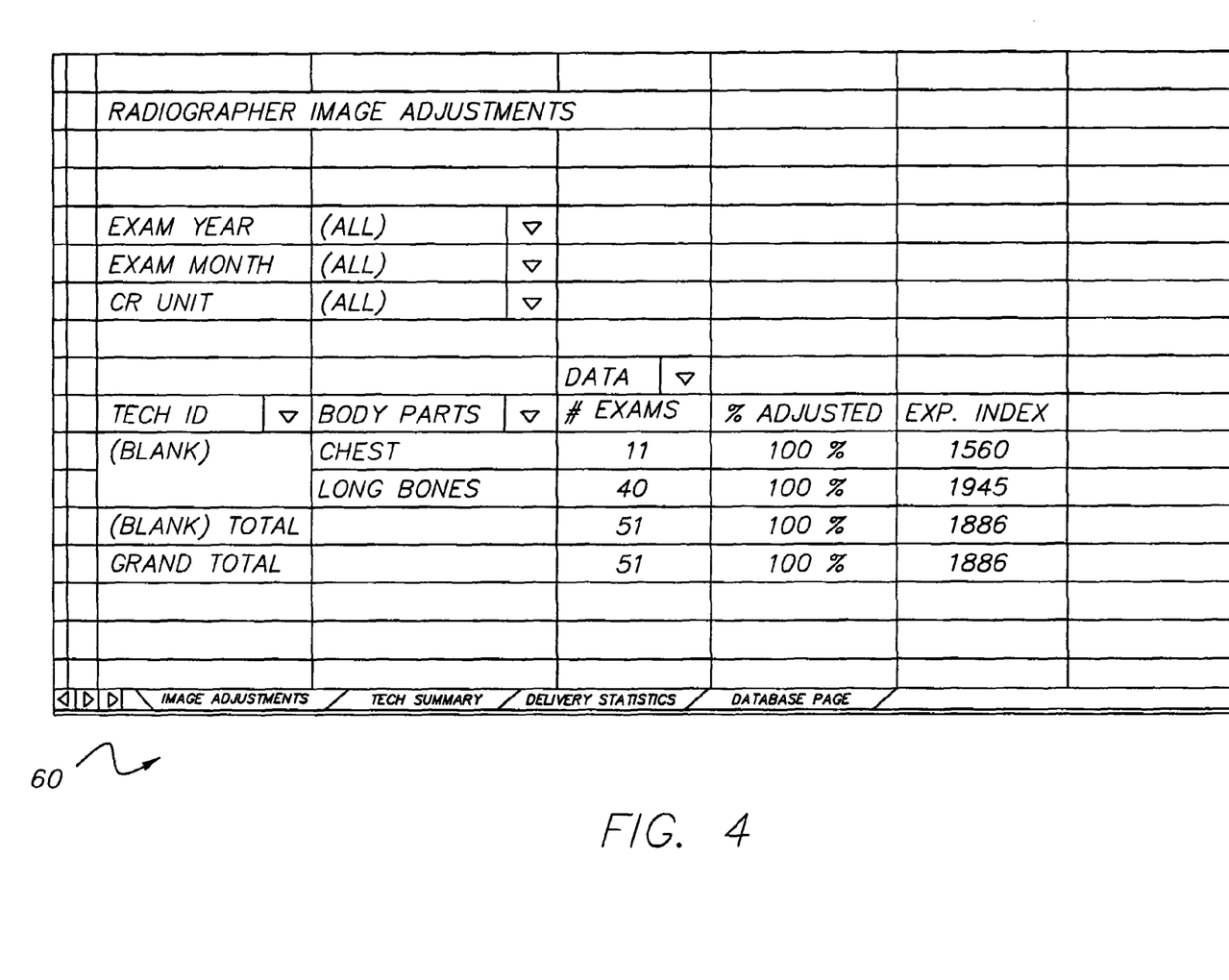
FIG. 4 is a diagrammatic view of a sample report relating to radiographer image adjustments.

FIG. 4 shows another sample report that can be produced by the present invention. As shown, the report 60 is of a radiographer's image adjustments. The report is for all of the exam years, all of the exam months and for all of the CR units. The Tech ID is left blank. For the body parts examined, 11 chest exams and 40 long bone exams were done. 100% of exams listed were adjusted and the mean Exposure Index for the Chest exams was 1560 and the mean Exposure index for the Long Bone exams was 1945. The total of exams for the Tech was 51, with 100% Adjusted and an Exposure Index of 1886. The Grand Total of exams was 51, with 100% Adjusted and Exposure Index of 1886.

Figure 5:
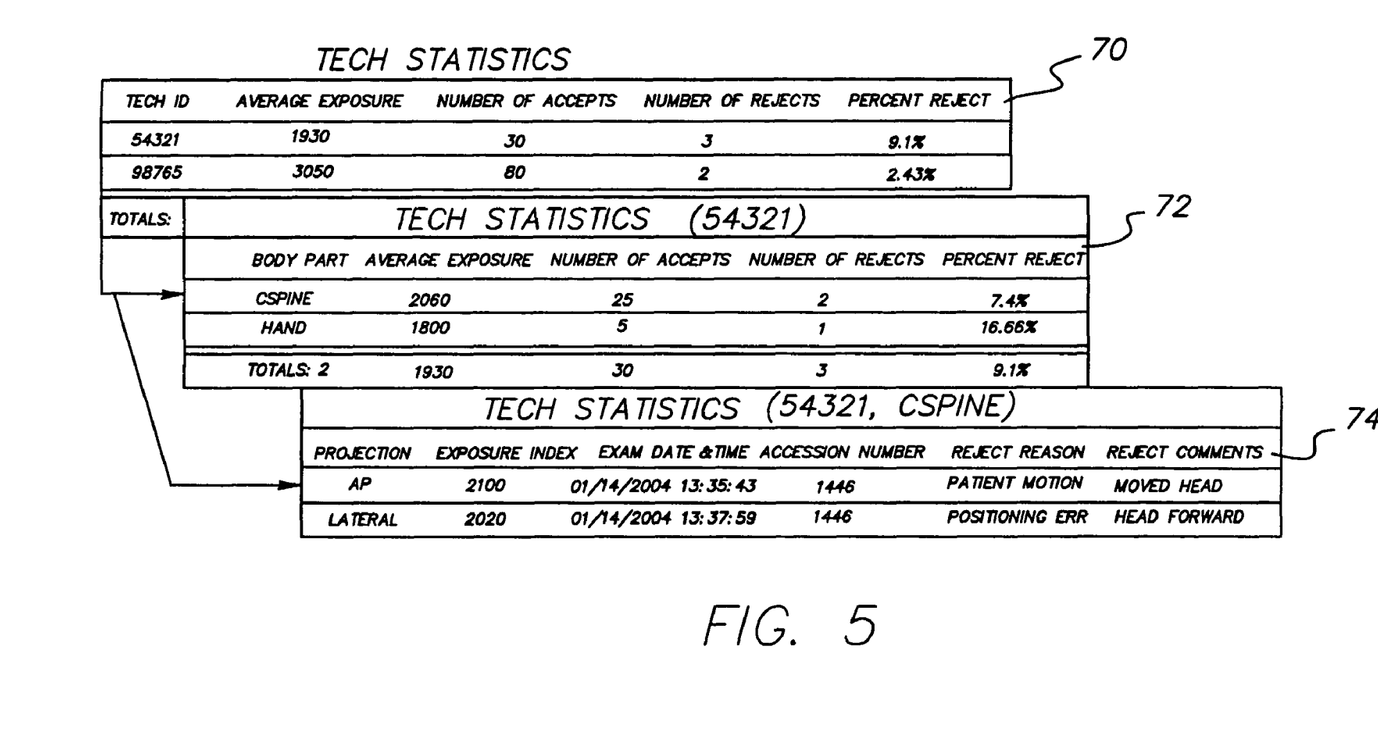
FIG. 5 is a diagrammatic view of a sample report illustrating reject reason analysis reporting.

FIG. 5 shows a series of reports that can be produced by the present invention relating to reject reason analysis reporting. As shown, report 70 includes Tech statistics for two techs showing average exposure, number of accepts, number of rejects and per cent reject for each tech. Report 72 includes more detailed statistics for one of the techs identified in report 70, including body part, average exposure, number of accepts, number of rejects, and per cent rejects for each body part. Report 74 gives further detail regarding the statistics for the C-spine rejections reported in report 72, including projection, exposure index, exam date and time, accession number, reject reason and reject comments.

In carrying out the present invention, an administrator or other key person logs onto computer 22 and opens an internet browser. The administrator then selects the radiographic systems which are in communication with computer 22 that have data to be included in a report. The computer software has several report templates, one or more of which are selected by the administrator. Computer 22 then collects data stored at the selected digital radiographic systems and produces one or more requested reports using a spreadsheet, such as, Microsoft's Excel. The present invention brings information relating to radiographic systems in the radiology department to an administrator's desktop, providing him with a digital dashboard for the management of quality metrics in general radiology. Exam information can be collected from all networked CR and DR systems and then downloaded into spreadsheets for viewing. The administrator is equipped with an efficient way to detect radiology department problems, provide appropriate solutions and monitor the results.

Any number or types of reports can be produced according to the invention, including one or more of the following:

Machine Use by Radiographer—Accumulates information for the specified period of time and reports the number of images (exams) by system by radiographer.

Exam Mix by Radiographer—Accumulates information for actual mix of procedures performed. There can be specified time period, radiographer, and system to filter the results.

Exam Mix by Radiographic System—Accumulates information for actual mix of procedures performed by radiographic system.

Exam Type by Radiographic System—Summarizes the exam by major body part by radiographic system.

Cassette Usage for CR Systems—Determines the total number of uses (exams) for each cassette among all the CR systems selected. Also identifies the repeat rate for images from each cassette. Cassettes listed in order, highest use to lowest use.

Cassette Use History for CR Systems—Displays the usage history of the cassette. Identifies the radiographer, patient ID and accession number for further investigation, if necessary.

Cassette Use Chart for CR Systems—A graph of cassette usage.

Repeat Analysis—Summary—Reports on the repeat rate by radiographer. Repeats are determined by the frequency of rejected images. Radiographers are listed in order, highest reject rate to lowest reject rate.

Repeat Analysis—Chart—A graph of repeat analysis by radiographer.

Repeat Analysis—By Exam Type—Reports on the repeat rate by exam type. Repeats are determined by the frequency of rejected images. Exam types (body part and projection) are listed in order, highest reject rate to lowest reject rate.

Repeat Images—by Exam and by Tech—Full detail report on the repeat rate by exam type by radiographer. Repeats are determined by the frequency of rejected images. Exam types (body part and projection) are listed in order, highest reject rate to lowest reject rate.

Reject Reasons—reports the frequency of repeat exams based on the reason provided by the radiographer.

Reject Comments—Reports the comments entered by radiographers when using the reject reason "other". (These are reasons other than default reasons, such as, clipped anatomy, patient motion, positioning error.) Each comment is associated with the body part and projection of the rejected image. Information can be filtered by year, month, or radiographic system.

Exposure Statistics—Two reports provide details on Exposure Index by radiographer and exam type. Both are displayed in descending order by Average Exposure Index. One report summarizes exposure index by radiographer and the other report provides more detail by exam type (body part and projection).

Radiographer Image Adjustments—Provides details of how frequently each radiographer made adjustments to the "window" and "level" of the image prior to releasing the image. Exposure index enables correlation between image adjustment and exposure level.

Radiographer Summary—Provides overall summary by radiographer on a single report. Details include number of images, repeat rate, average exposure index, and frequency of adjusting image brightness and contrast.

Image Delivery Statistics—Provides details on the various destinations to which radiographic images were delivered.

Although the present invention has been described in relation to a radiology department, wherein a number of radiographic systems communicate with a central administrator's computer, it will be understood that the term department is not meant to be limiting and any network or cluster of radiographic systems that communicate with a central computer incorporating the present invention is deemed to be within the scope thereof. Moreover, although the radiographic systems described in the description of the invention are CR or DR systems, it will be understood that the present invention can also be used with other digital radiographic systems, such as, Ultrasound systems, CT systems, MRI systems, PET systems, industrial radiographic systems, dental radiographic systems, or the like. It will also be appreciated that the administrator's computer need not be a stand alone computer, but may be integral with one of the radiographic systems. In such case it is only necessary that the other radiographic systems be in communication with such system.

The invention has been described in detail with particular reference to certain preferred embodiments thereof, but it will be understood that variations and modifications can be effected within the spirit and scope of the invention.

The invention claimed is:

1. A system for producing administrative reports for a digital radiology department comprising:
   a plurality of digital radiographic systems, each of which has storage for storing digital data in html relating to the operation and/or use of the system; and
   a computer in communication with the plurality of digital radiographic systems, wherein the computer has a web browser for collecting digital data relating to the operation and/or use of each the digital radiographic systems, and wherein the computer produces one or more administrative reports based on the collected data, wherein the digital data stored by the digital radiographic systems is repeat analysis data, wherein a repeat analysis report is provided as one of the administrative reports, wherein the repeat analysis report includes repeat rate compiled by examination type and compiled by radiographer and listed in a sequenced reject rate order, wherein repeats are determined by a frequency of rejected images, and wherein the examination type includes body part and projection,
   wherein the repeat analysis report includes a tiered reject analysis report, the tiered reject analysis report including a first report including radiographer statistics for a plurality of radiographers, the first report providing average exposure, number of accepts, and number of rejects received from more than one of the plurality of digital radiographic systems for at least one radiographer of the plurality of radiographers, a second report for said at least one radiographer in the first report, the second report to include statistics for one radiographer including one of a plurality of body parts, average exposure, number of accepts, and number of rejects, for each body part, and a third report for said each body part in the second report, the third report to include statistics for a corresponding body art rejection including projection exposure index, exam date and time, and reject reason or reject comments, wherein said repeats are determined by said frequency of rejected images.

2. The system of claim 1 wherein the produced reports are displayed on an electronic display.

3. The system of claim 1 wherein the plurality of digital radiographic systems includes one or more of one of a computed radiography system and a direct radiography system.

4. The system of claim 1 wherein the plurality of digital radiographic systems includes one or more of one of an ultrasound system, a CT system, an MRI system, a PET system, an industrial radiographic system, and a dental radiographic system.

5. The system of claim 1, wherein another administrative report includes percentage of all images that received image adjustments provided by machine and radiographer.

6. The system of claim 1 wherein the digital data stored by the digital radiographic systems is exposure level data and wherein the produced report summarizes at least some or all of the collected exposure level data.

7. The system of claim 1 wherein the digital data stored by the digital radiographic systems is device usage data and wherein the produced report summarizes at least some or all of the collected device usage data.

8. The system of claim 1 wherein the digital data stored by the digital radiographic systems is equipment quality data and wherein the produced report summarizes at least some or all of the collected equipment quality data, wherein the collected equipment quality data is device specific data including Modulation Transfer Function (MTF) data, Detective Quantum Efficiency (DQE) data, and pixel dropout data.

9. The system of claim 1 wherein the produced report is one or more of the following: system use by radiographer, exam mix by radiographer, exam mix by digital radiographic system, exam type by digital radiographic system, cassette usage for CR systems, cassette use history by CR systems, cassette use chart for CR systems, repeat analysis summary, repeat analysis chart, repeat analysis by exam type, repeat images by exam and by technologist, reject reasons, reject comments, exposure index statistics by radiographer and by exam type, radiographer image adjustments, radiographer summary, and image delivery statistics.

10. A system for producing administrative reports for a digital radiology department comprising:
a plurality of digital radiographic systems, each of which has storage for storing digital data in html relating to the operation and/or use of the system, including one or more of repeat analysis data, exposure level data, device usage data, equipment quality data; and
a computer in communication with the plurality of digital radiographic systems, wherein the computer has a web browser for collecting digital data relating to the operation of each the digital radiographic systems, and wherein the computer produces one or more administrative reports based on the collected data, including a report summarizing at least some or all of the repeat analysis data, and one or more of the following, a report summarizing at least some or all of the exposure level data, a report summarizing at least some or all of system usage data, and a report summarizing at least some or all of the equipment quality data, wherein the repeat analysis report includes a cassette usage report for computed radiography (CR) systems, the cassette usage report including a total number of examination uses for each cassette used at a plurality of CR systems of the plurality of digital radiographic systems and identifying a repeat rate for images from said each cassette, wherein cassettes listed in a listed in a sequenced reject rate order, wherein repeats are determined by a frequency of rejected images,
wherein the repeat analysis report includes a tiered reject analysis report, the tiered reject analysis report including a first report including radiographer statistics for a plurality of radiographers, the first report providing average exposure, number of accepts, and number of rejects received from more than one of the plurality of digital radiographic systems for at least one radiographer of the plurality of radiographers, a second report for said at least one radiographer in the first report, the second report to include statistics for one radiographer including one of a plurality of body parts, average exposure, number of accepts, and number of rejects, for each body part, and a third report for said each body part in the second report, the third report to include statistics for a corresponding body part rejection including projection, exposure index, exam date and time, and reject reason or reject comments, wherein said repeats are determined by said frequency of rejected images.

11. A method of producing an administrative report for a digital radiology department comprising;
providing a plurality of digital radiographic systems, and storing digital data in html at each of the systems relating to the operation and use of the system;
using a computer which is in communication with the plurality of digital radiographic systems, to collect, by means of a web browser, digital data relating to the operation and/or use of each of the digital radiographic systems; and to produce one or more administrative reports based on the collected data;
wherein the digital data stored by the digital radiographic systems is repeat analysis data, wherein a repeat analysis report is provided as one of the administrative reports, wherein the repeat analysis report includes repeat rate compiled by examination type and compiled by radiographer and listed in a sequenced reject rate order, and
wherein the repeat analysis report includes a tiered reject analysis report, the tiered reject analysis report including a first report including radiographer statistics for a plurality of radiographers, the first report providing average exposure, number of accepts, and number of rejects received from more than one of the plurality of digital radiographic systems for at least one radiographer of the plurality of radiographers, a second report for said at least one radiographer in the first report, the second report to include statistics for one radiographer including one of a plurality of body parts, average exposure, number of accepts, and number of rejects, for each body part, and a third report for said each body part in the second report, the third report to include statistics for a corresponding body part rejection including projection, exposure index, exam date and time, and reject reason or reject comments, wherein said repeats are determined by said frequency of rejected images.

12. The system of claim 1, wherein a reject reason report includes a frequency of repeat examinations based on a radiographer reason including clipped anatomy, patient motion, positioning error and radiographer comment.

13. The system of claim 1, wherein the sequenced reject rate order comprises highest reject rate to lowest reject rate, and wherein radiographers are listed in the highest reject rate to lowest reject rate order.

14. The system of claim 1, wherein the repeat analysis report having the repeat rate by the radiographer includes the repeats from a plurality of the digital radiographic systems, and wherein the computer is in one of the digital radiographic systems.

15. The method of claim 11, wherein the repeat analysis report includes a cassette usage report for computed radiography (CR) systems, the cassette usage report including a total number of examination uses for each cassette used at a plurality of CR systems of the plurality of digital radiographic systems and identifying a repeat rate for images from said each cassette, wherein cassettes listed in a listed in a sequenced reject rate order, wherein said repeats are determined by said frequency of rejected images.

\* \* \* \* \*